United States Patent
Weber et al.

(10) Patent No.: US 7,147,644 B2
(45) Date of Patent: Dec. 12, 2006

(54) APPARATUS FOR DELIVERY OF OCULAR IMPLANTS

(75) Inventors: David Weber, Danville, CA (US); Ingrid Kane, Los Altos, CA (US); Mike Rehal, Boulder Creek, CA (US); Robert L. Lathrop, III, Santa Clara, CA (US); Kenny Aptekarev, Santa Cruz, CA (US)

(73) Assignee: Allergan, Inc., Irvine, CA (US)

( * ) Notice: Subject to any disclaimer, the term of this patent is extended or adjusted under 35 U.S.C. 154(b) by 297 days.

(21) Appl. No.: 10/853,584

(22) Filed: May 24, 2004

(65) Prior Publication Data

US 2004/0215133 A1    Oct. 28, 2004

Related U.S. Application Data

(62) Division of application No. 10/246,884, filed on Sep. 18, 2002, now Pat. No. 6,899,717.

(51) Int. Cl.
    *A61F 9/00*    (2006.01)
(52) U.S. Cl. ..................................... 606/107
(58) Field of Classification Search ............... 606/107, 606/108, 167, 181, 182, 185; 623/4.1, 5.11, 623/6.11, 6.12
    See application file for complete search history.

(56) References Cited

U.S. PATENT DOCUMENTS

| | | | |
|---|---|---|---|
| 3,220,413 A | 11/1965 | Sunnen | |
| 3,238,941 A | 3/1966 | Klein et al. | |
| 3,698,390 A | 10/1972 | Ferris | |
| 3,937,370 A | 2/1976 | Witty | |
| 4,144,317 A | 3/1979 | Higuchi et al. | 424/21 |
| 4,597,753 A | 7/1986 | Turley | |
| 4,659,326 A * | 4/1987 | Johnson et al. | 604/62 |
| 4,668,506 A | 5/1987 | Bawa | 424/429 |
| 4,799,478 A | 1/1989 | Fedorov et al. | |
| 4,850,970 A | 7/1989 | Sutherland | |
| 4,853,224 A | 8/1989 | Wong | 424/427 |
| 4,900,304 A | 2/1990 | Fujioka et al. | |
| 4,907,587 A | 3/1990 | Fedorov et al. | |
| 4,915,686 A | 4/1990 | Frederick | |
| 4,919,130 A * | 4/1990 | Stoy et al. | 606/107 |
| 4,959,217 A | 9/1990 | Sanders et al. | 424/473 |
| 4,997,652 A | 3/1991 | Wong | 424/428 |
| 5,014,717 A | 5/1991 | Lohrmann | |
| 5,059,172 A | 10/1991 | Sutherland et al. | |
| 5,098,443 A | 3/1992 | Parel et al. | |

(Continued)

FOREIGN PATENT DOCUMENTS

EP    0415504    8/1990

(Continued)

OTHER PUBLICATIONS

Cheng, Cheng-Kuo et al., *Intravitreal Sustained-Release Dexamethasone Device in the Treatment of Experimental Uveitis*, Investigative Ophthalmology & Visual Science, Feb. 1995, vol. 36, No. 2, pp. 442-453.

(Continued)

*Primary Examiner*—Kevin T. Truong
(74) *Attorney, Agent, or Firm*—Stephen Donovan

(57) ABSTRACT

An apparatus and methods for delivering ocular implants or microimplants. The apparatus is ergonomically designed for ease of use, and a simple manual depression of an actuator produces proportional movement of a linkage causing the implant or microimplant to be ejected through a cannula disposed at the desired location in the eye. Small gauge cannulas are provided for self-sealing methods of delivery.

21 Claims, 10 Drawing Sheets

U.S. PATENT DOCUMENTS

| | | | |
|---|---|---|---|
| 5,164,188 A | 11/1992 | Wong | 424/428 |
| 5,250,026 A | 10/1993 | Ehrlich et al. | |
| 5,279,554 A | 1/1994 | Turley | |
| 5,284,479 A | 2/1994 | De Jong | |
| 5,336,206 A | 8/1994 | Shichman | |
| 5,378,475 A | 1/1995 | Smith et al. | 424/473 |
| 5,439,473 A * | 8/1995 | Jorgensen | 606/182 |
| 5,443,505 A | 8/1995 | Wong et al. | 623/4 |
| 5,451,213 A | 9/1995 | Teicher et al. | |
| 5,466,233 A | 11/1995 | Weiner et al. | 604/890.1 |
| 5,476,511 A | 12/1995 | Gwon et al. | 623/4 |
| 5,725,521 A | 3/1998 | Mueller | |
| 5,807,400 A | 9/1998 | Chambers et al. | |
| 5,824,001 A | 10/1998 | Erskine | |
| 5,824,072 A | 10/1998 | Wong | 623/4 |
| 5,860,984 A * | 1/1999 | Chambers et al. | 606/107 |
| 5,876,373 A | 3/1999 | Giba et al. | |
| 5,941,250 A | 8/1999 | Aramant et al. | |
| 5,957,892 A | 9/1999 | Thorne | |
| 6,117,443 A | 9/2000 | Cherif-Cheikh | |
| 6,120,786 A | 9/2000 | Cherif-Cheikh | |
| 6,142,972 A | 11/2000 | Cheikh | |
| 6,159,218 A | 12/2000 | Aramant et al. | |
| 6,190,350 B1 | 2/2001 | Davis et al. | |
| 6,217,895 B1 | 4/2001 | Guo et al. | 424/427 |
| 6,514,270 B1 * | 2/2003 | Schraga | 606/182 |
| 6,548,078 B1 | 4/2003 | Guo et al. | 424/423 |

FOREIGN PATENT DOCUMENTS

| | | |
|---|---|---|
| EP | 0544948 B1 | 9/1995 |
| WO | WO 99/33512 | 7/1999 |
| WO | WO 99/53991 | 10/1999 |

OTHER PUBLICATIONS

Enyedi, Laura et al., *An Intravitreal Device Providing Sustained Release of Cyclosporine and Dexamethasone*, Current Eye Research (1995) pp. 549-557.

Hainsworth, Dean P. et al., *Sustained Release Intravitreal Dexamethasone*, Journal of Ocular Pharmacology and Therapeutics, (1996) vol. 12, No. 1, pp. 57-63.

Kochinke, F. et al., *Biodegradable Drug Delivery System for Uveitis Treatment*, Investigative Ophthalmology & Visual Science, Feb. 15, 1996, vol. 37. No. 3, 186-B98.

* cited by examiner

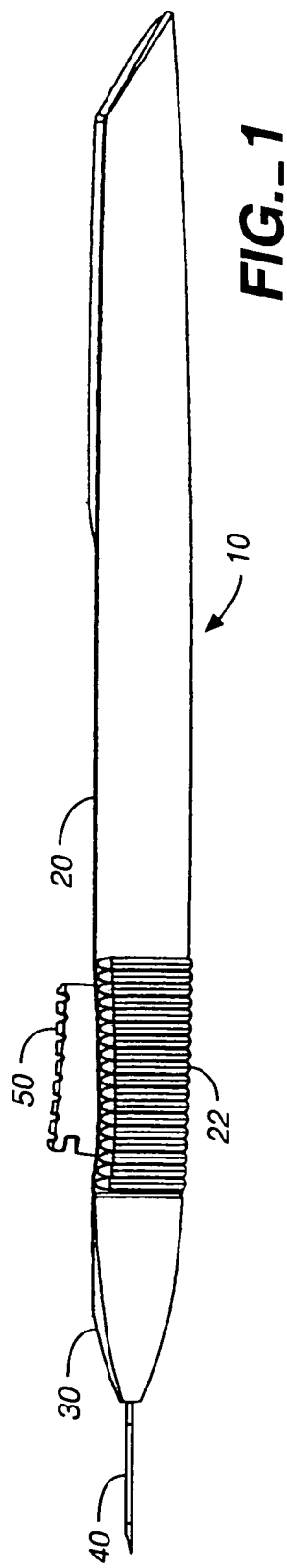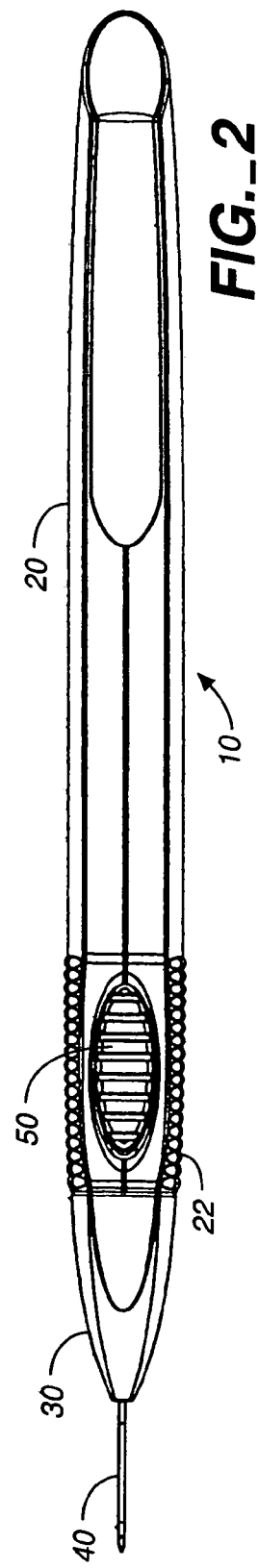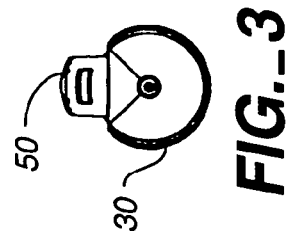

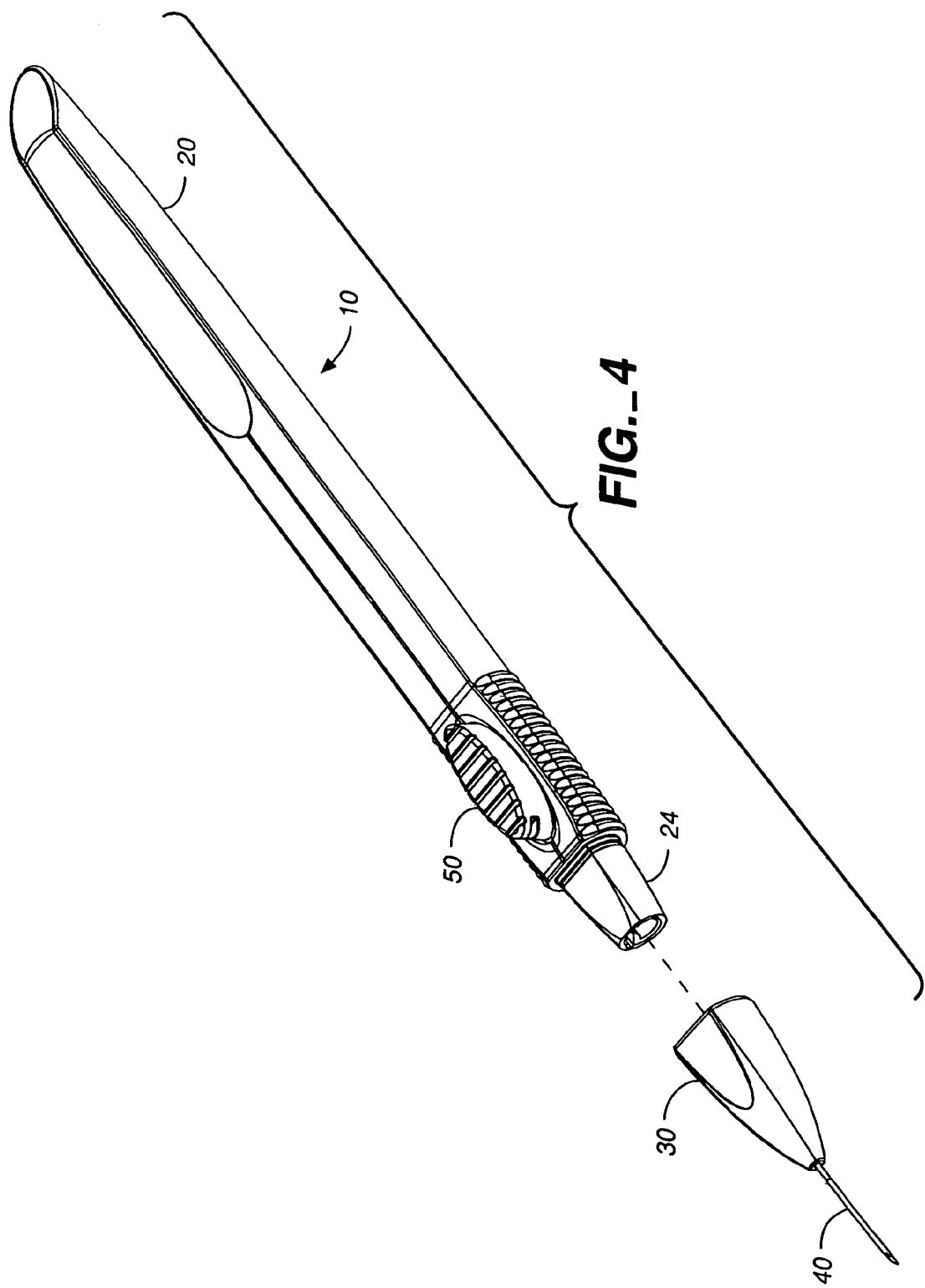
FIG._4

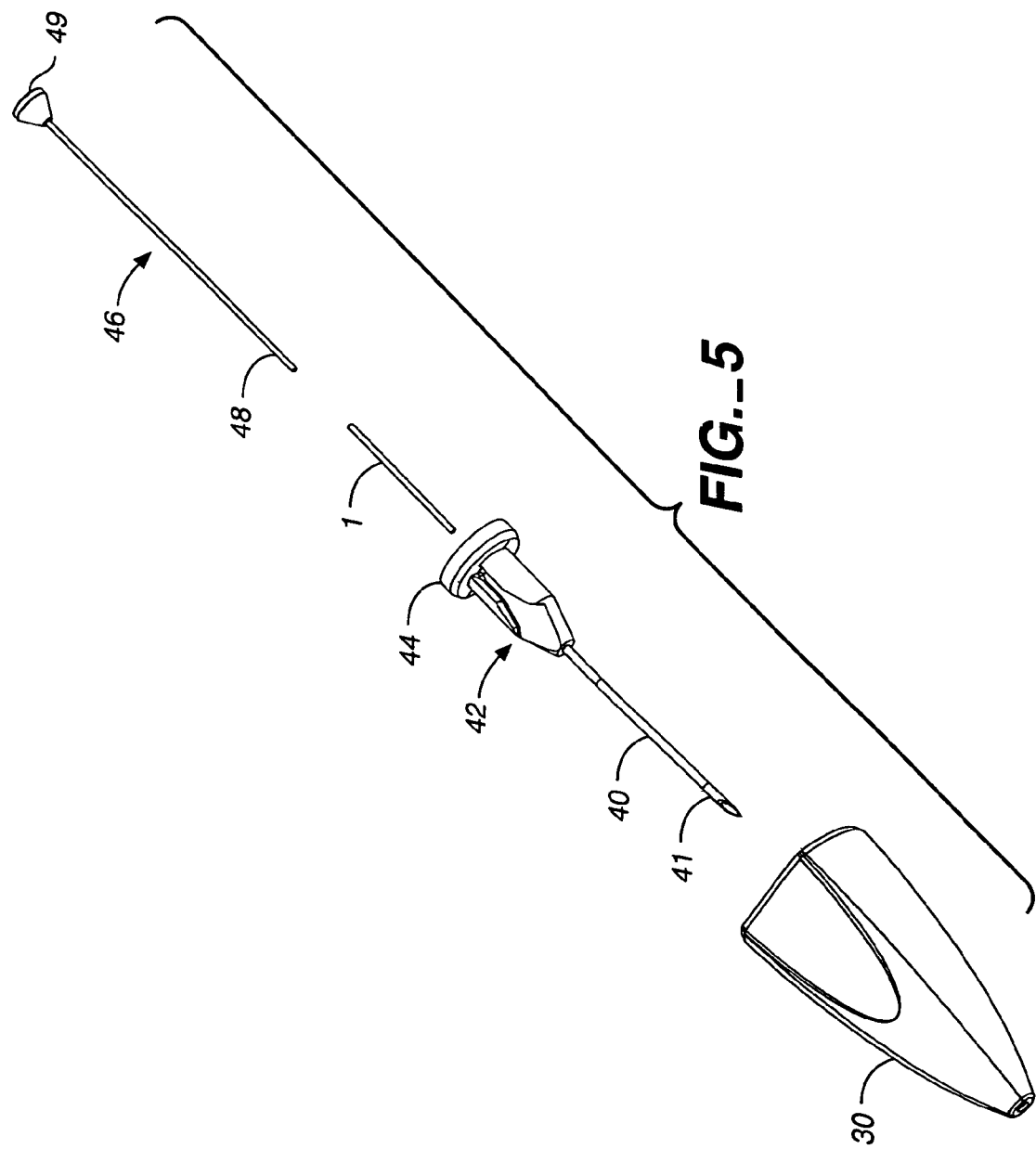

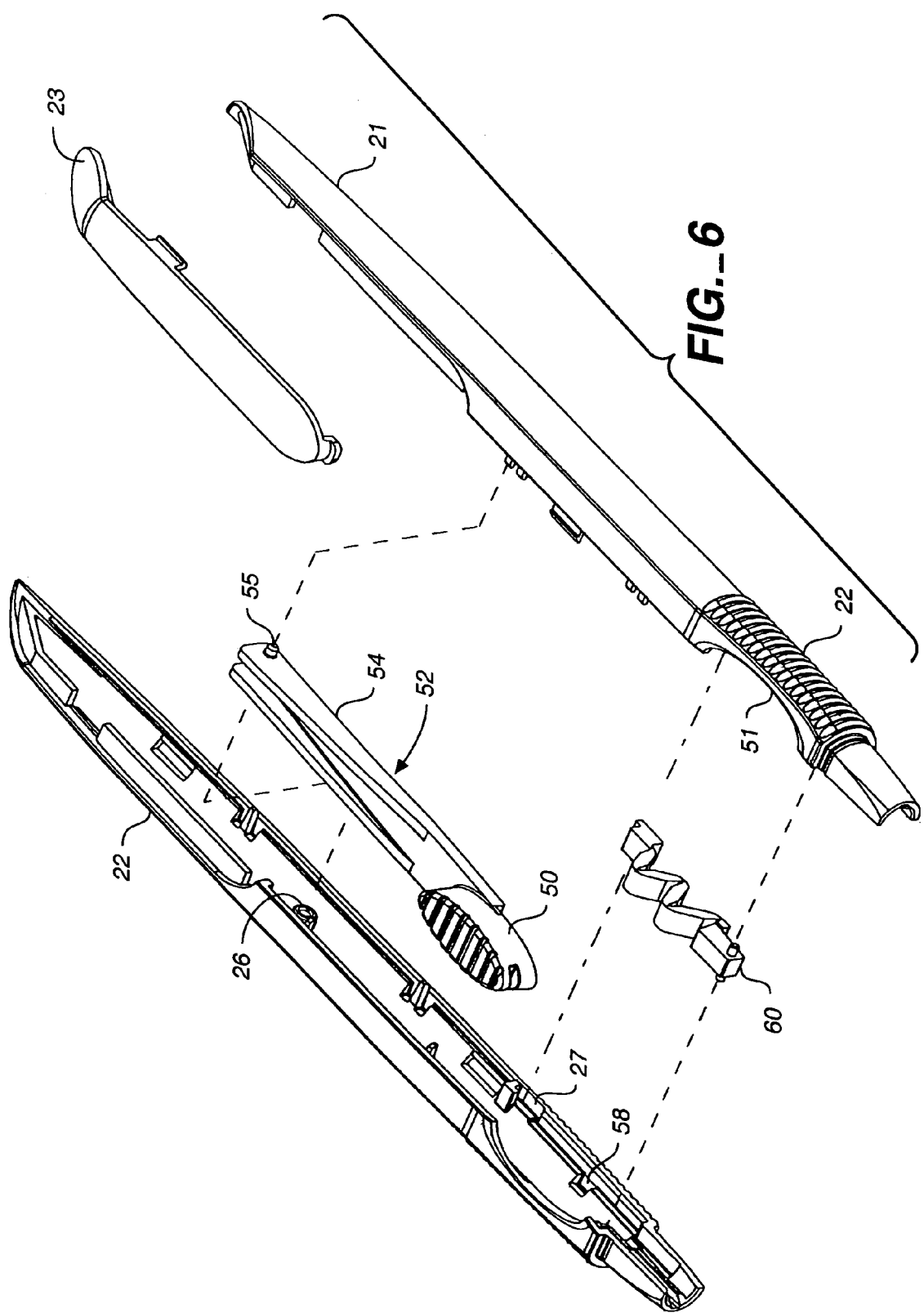
FIG._6

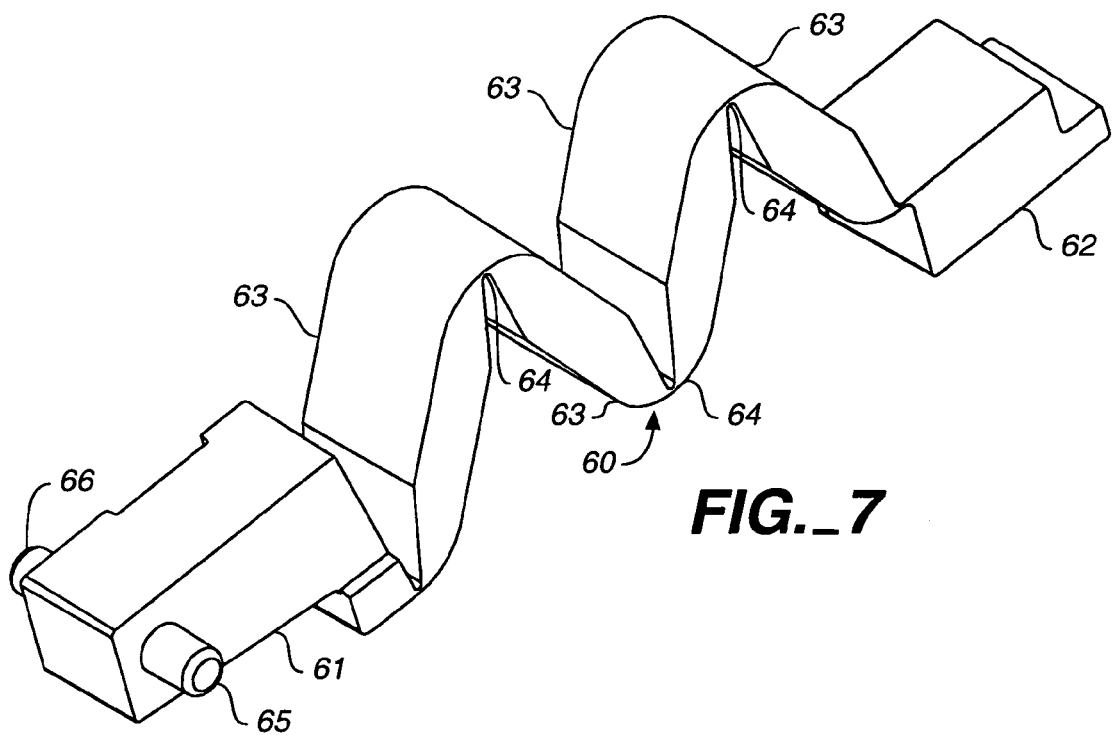
FIG._7
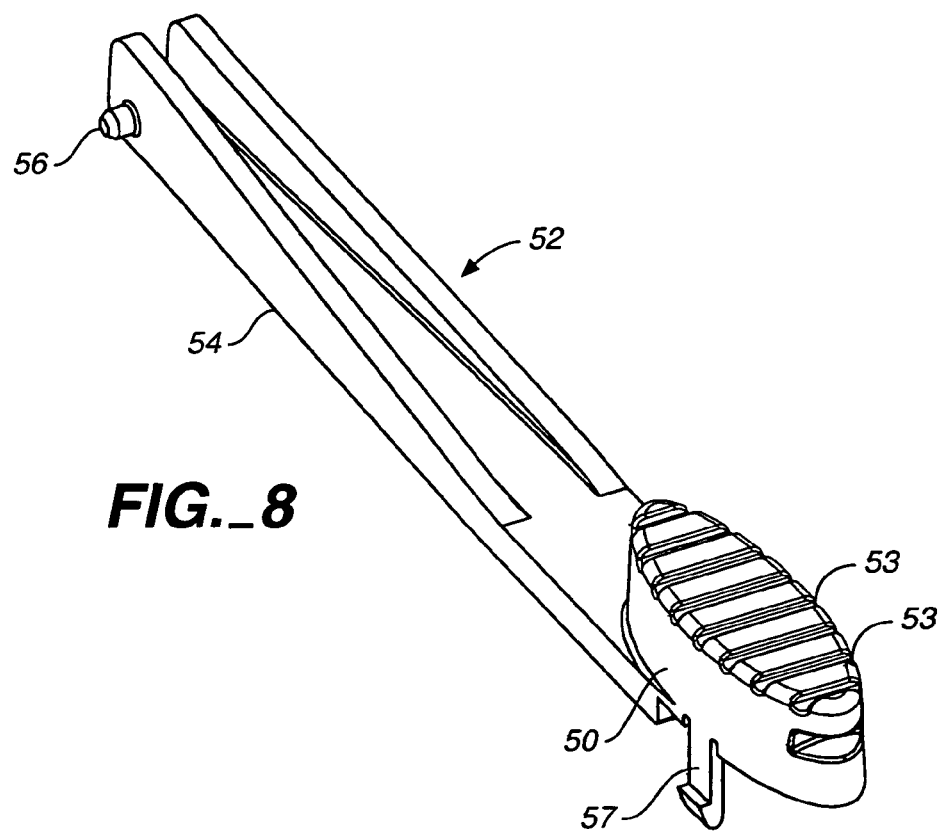
FIG._8

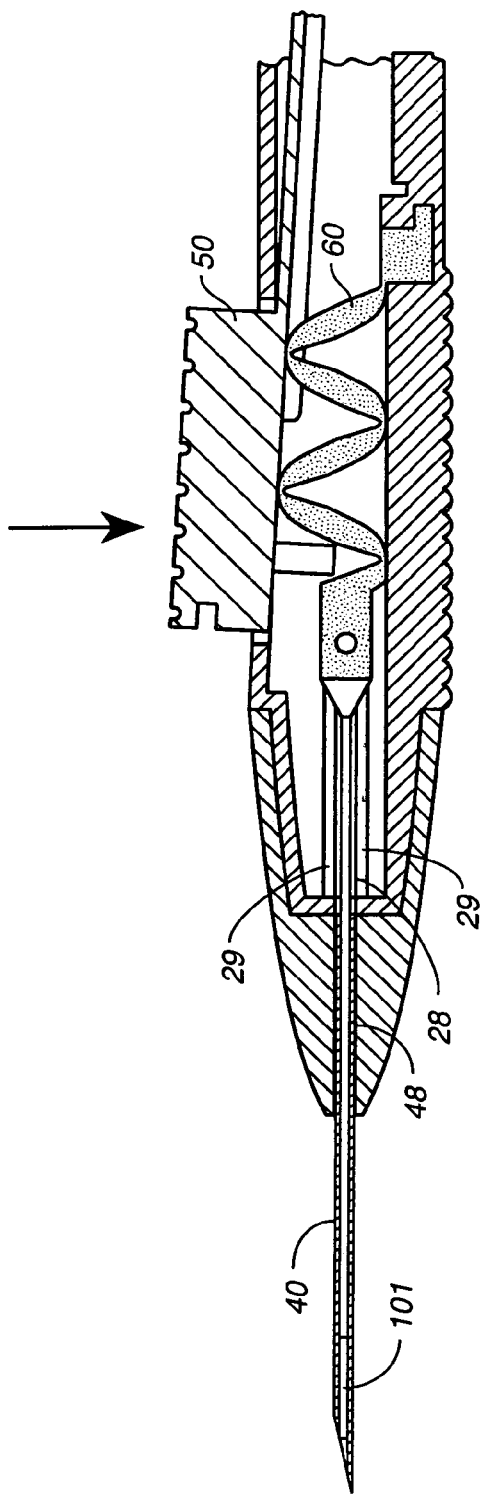
FIG._9A
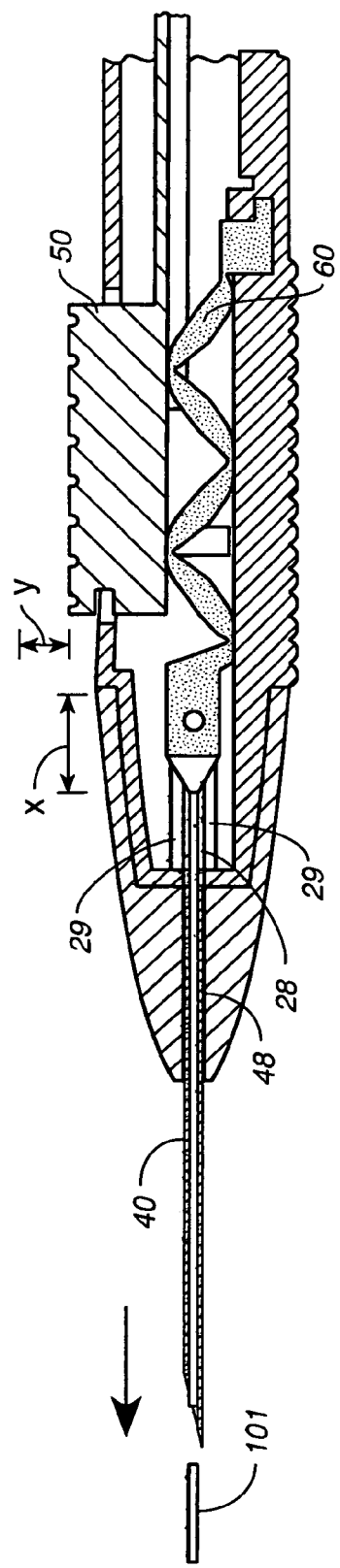
FIG._9B

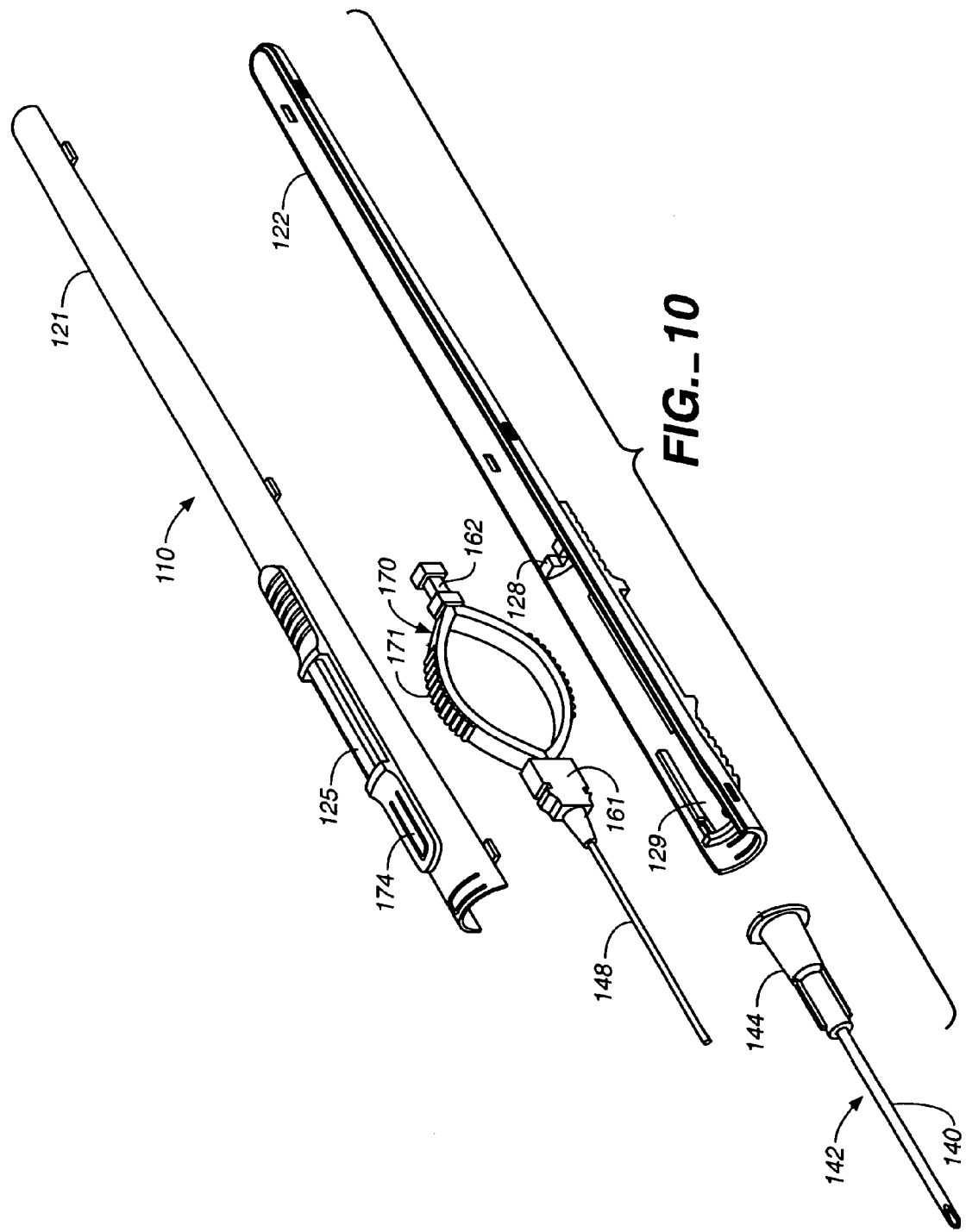
FIG._10

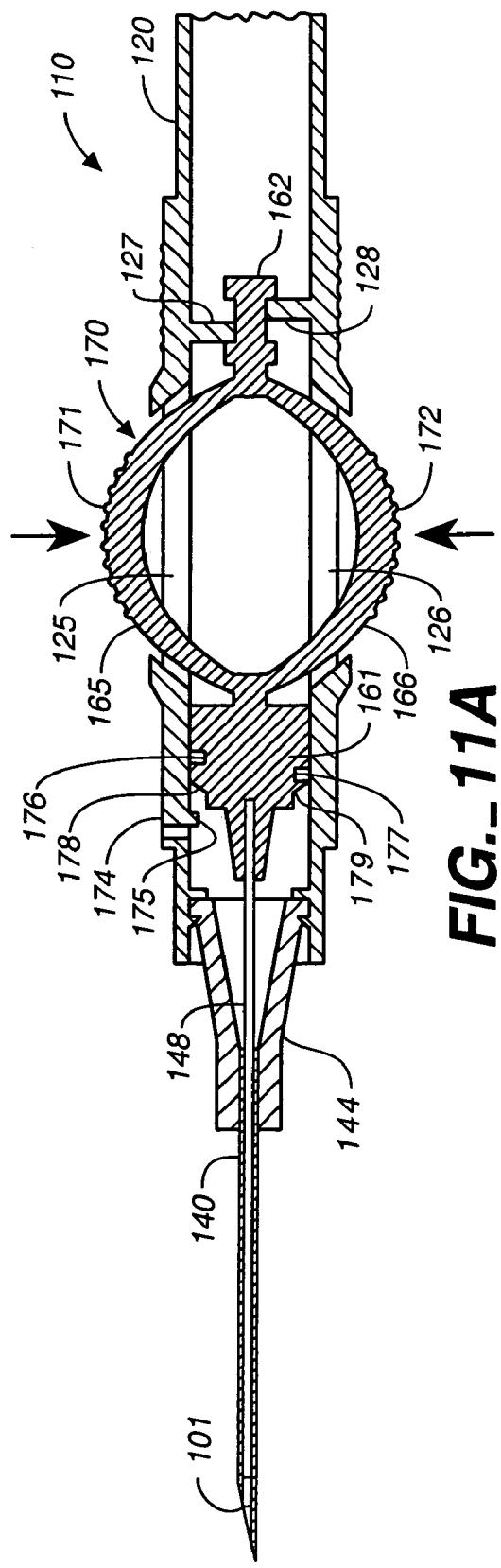
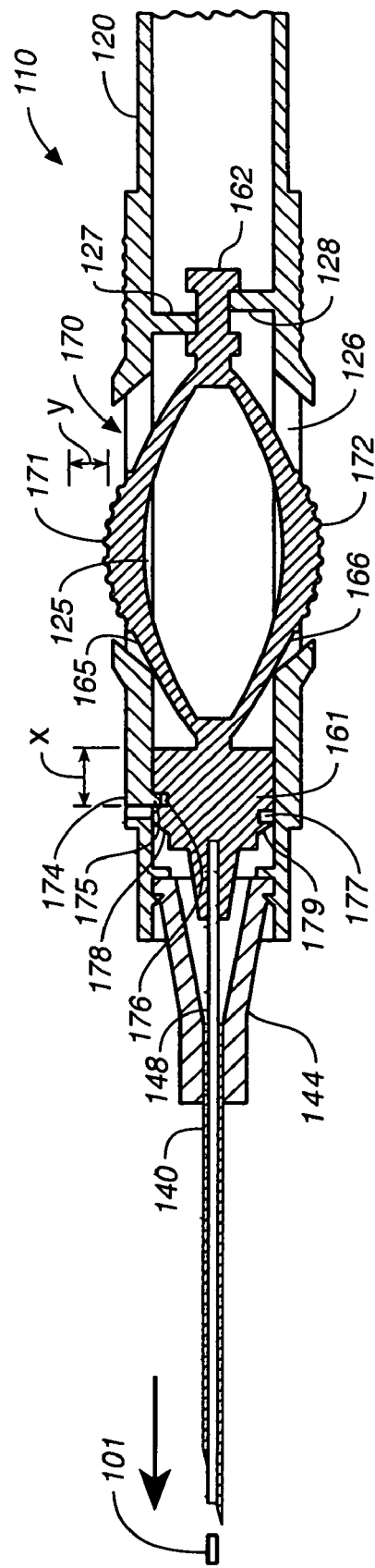
FIG._11A
FIG._11B

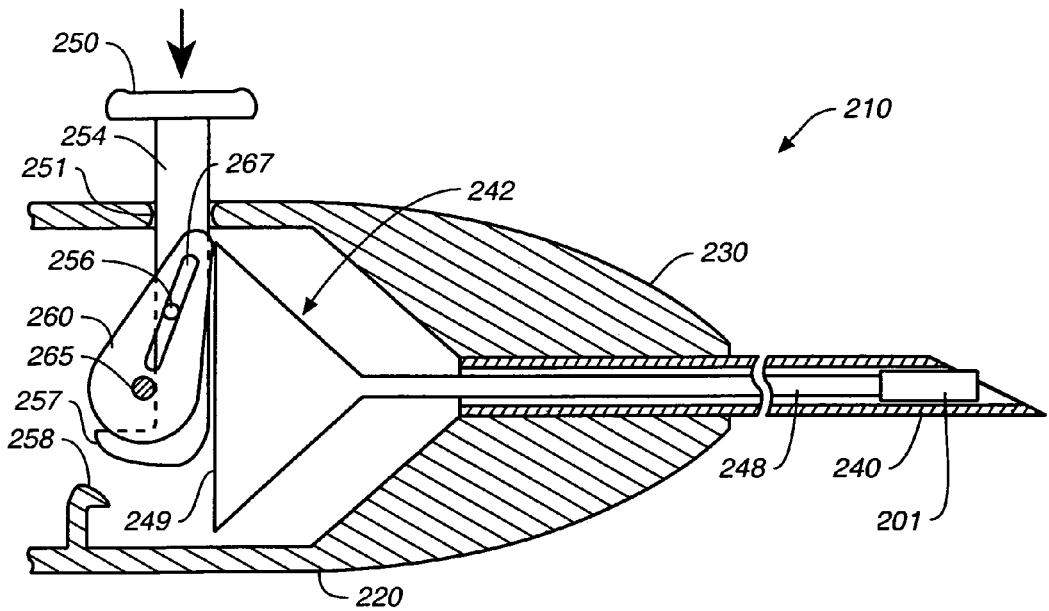
FIG._12A
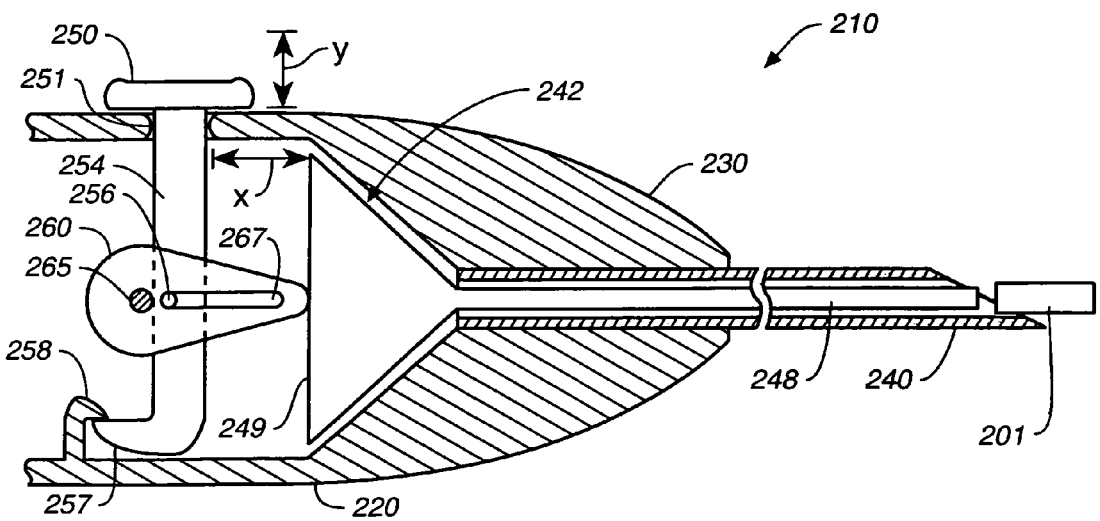
FIG._12B

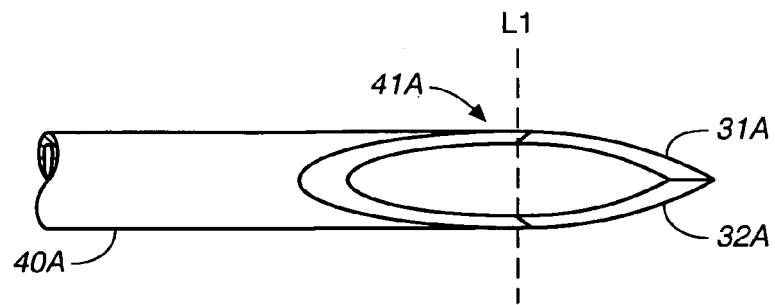
FIG._13A
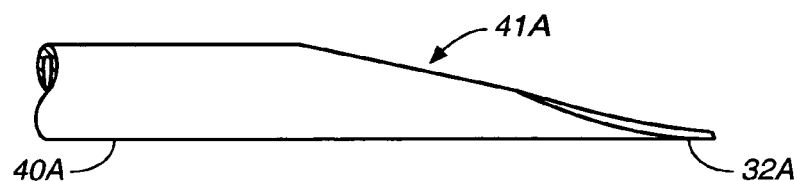
FIG._13B
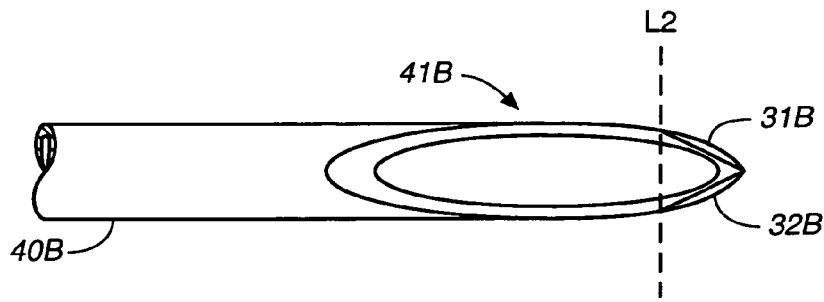
FIG._14A
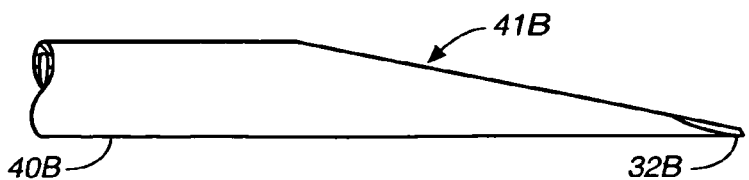
FIG._14B

APPARATUS FOR DELIVERY OF OCULAR IMPLANTS

CROSS REFERENCE

This application is a divisional of application Ser. No. 10/246,884, filed Sep. 18, 2002 now U.S. Pat. No. 6,899,717.

TECHNICAL FIELD

The present invention relates to methods and apparatus for delivering solid or semi-solid materials into the eye. Specifically, the methods and apparatus can be used to introduce implants containing therapeutic or active agents, including bioerodible implants, into various locations within the eye, including the vitreous of the eye.

BACKGROUND ART

A primary difficulty in treating diseases of the eye is the inability to introduce drugs or therapeutic agents into the eye and maintain these drugs or agents at a therapeutically effective concentration in the eye for the necessary duration. Systemic administration may not be an ideal solution because, often, unacceptably high levels of systemic dosing is needed to achieve effective intraocular concentrations, with the increased incidence of unacceptable side effects of the drugs. Simple ocular instillation or application is not an acceptable alternative in many cases because the drug may be quickly washed out by tear-action or is otherwise depleted from within the eye into the general circulation. Suprachoroidal injections of drug solutions have also been performed, but again the drug availability is short-lived. Such methods make it difficult to maintain therapeutic levels of drug for adequate time periods.

Efforts to address this problem have lead to the development of drug delivery devices, or implants, which can be implanted into the eye such that a controlled amount of desired drug can be released constantly over a period of several days, or weeks, or even months. Many such devices have been previously reported. See, for example, U.S. Pat. No. 4,853,224, which discloses biocompatible implants for introduction into an anterior segment or posterior segment of an eye for the treatment of an ocular condition. U.S. Pat. No. 5,164,188 discloses a method of treating an ocular condition by introduction of a biodegradable implant comprising drugs of interest into the suprachoroidal space or pars plana of the eye. See also U.S. Pat. Nos. 5,824,072, 5,476,511, 4,997,652, 4,959,217, 4,668,506, and 4,144,317. Other methods include anchoring a plug or tack containing a drug into the sclera of the eye (see, e.g., U.S. Pat. No. 5,466,233).

Various sites exist in the eye for implantation of a drug delivery device or implant, such as the vitreous of the eye, anterior or posterior chambers of the eye, or other areas of the eye including intraretinal, subretinal, intrachoroidal, suprachoroidal, intrascleral, episcleral, subconjunctival, intracorneal or epicorneal spaces. Wherever the desired location of implantation, typical methods of implantation all require relatively invasive surgical procedures, pose a risk of excessive trauma to the eye, and require excessive handling of the implant. For example, in a typical method for placement in the vitreous, an incision is made through the sclera, and the implant is inserted into and deposited at the desired location in the vitreous, using forceps or other like manual grasping device. Once deposited, the forceps (or grasping device) is removed, and the incision is sutured closed. Alternatively, an incision can be made through the sclera, a trocar can be advanced through the incision and then the implant can be delivered through the trocar. Similar methods can be employed to deliver implants to other locations, e.g., implantation in the anterior chamber of the eye through an incision in the cornea.

The drawbacks of such techniques for implant delivery are many-fold. Extensive handling of the implant is necessitated in these techniques, creating a risk that the implant will be damaged in the process. Many such implants are polymer-based and are relatively fragile. If portions of such implants are damaged and broken-off, the effective therapeutic dose delivered by the implant once placed will be significantly altered. In addition, it becomes inherently difficult using these methods to achieve reproducible placement from patient to patient. Also of import is that fact that all such techniques require an incision or puncture in the eye large enough to require suturing. Thus such techniques are typically performed in a surgical setting.

There thus remains a need for a more facile, convenient, less invasive, and less traumatic means for delivering implants into the eye. There also remains a need for a more controlled means of delivering implants into the eye.

SUMMARY OF THE INVENTION

The present invention meets these and other needs and provides methods and apparatus for easily, safely, and more precisely delivering an implant into the eye.

In one aspect of the invention, an apparatus is provided having an elongate housing with a cannula extending longitudinally from the housing. The cannula includes a lumen extending through the length of the cannula, such that an ocular implant can be received within the cannula lumen. A plunger having a push rod is also received within the cannula lumen and is capable of movement from a first to second position within the lumen. A linkage is provided having a moveable end engageable with the plunger, and a fixed end secured to the housing. The moveable end of the linkage is capable of movement from a first to second position relative to the housing upon application to the linkage of a force normal to the housing axis. When such a force is applied the plunger moves from the first to the second position within the cannula, forcing an implant retained within the cannula to be ejected.

In one embodiment, the apparatus further includes an actuating lever with one end pivotally mounted within mounted the housing and the other end of the lever engaged with the linkage. The actuating lever can further be configured for manual accession, such that manual depression of the lever against the linkage provides the force normal to the housing axis which causes translational motion of the moveable end of the linkage along the housing axis and subsequent movement of the plunger and ejection of the implant. The linkage itself can further include a series of flexibly joined segments.

In another embodiment, the apparatus includes a linkage that includes one or more flexible bow elements. The bow element or elements can further include a portion or portions that extend from the housing for manual accession, such that manual depression of the portion or portions provides the normal force to the housing axis to cause translational motion of the linkage.

In a further embodiment, the apparatus includes an actuating lever operably linked to a linkage comprising a can assembly. The actuating lever can be oriented for movement in a direction normal to the housing axis and can be further configured for manual accession. Manual depression of the lever causes rotation of the cam assembly about a fixed pivot point resulting in engagement of the cam assembly with the plunger and subsequent movement of the plunger to eject the implant.

In yet another embodiment, the cannula is further configured to have an outer diameter of 0.032 inches or less. In further embodiments, the cannula is configured to have an outer diameter of 0.028 inches or less or 0.025 inches or less. Alternatively, in cases where the cannula has a non-circular cross-section, the cannula can have a cross-sectional area of up to 0.0008 square inches or more, depending on the particular cross-sectional geometry. Cannulas having such configurations are able to receive and deliver smaller ocular implants, i.e., so-called microimplants.

The invention also provides methods of delivery of an implant into a location of the eye. In one aspect of the invention, a cannula is used having an outer diameter of 0.032 inches or less. In other aspects of the invention, a cannula is used having an outer diameter of 0.028 inches or less or 0.025 inches or less. In yet another aspect of the invention, in cases where the cannula has a non-circular cross-section, the cannula has a cross-sectional area of up to 0.0008 square inches or more, depending on the particular cross-sectional geometry. The use of cannulas having such cross-sectional dimensions allows for self-sealing methods of implant delivery.

Accordingly, in one embodiment, a method of delivering an ocular microimplant into a patient's eye is provided which involves providing a cannula having a distal sharpened tip, lumen extending through the cannula, a microimplant retained within the lumen, and a push rod received through a proximal end of the cannula. The cannula is then used to puncture through the outer layer of a patient's eye with the cannula and inserted to a desired location within the patient's eye to a desired location. Once the cannula is positioned, the push rod is moved from the proximal end of the cannula toward the distal end of the cannula, thereby ejecting the microimplant from the cannula. After ejection, the cannula and push rod are removed from the patient's eye, and the puncture created by the insertion of the cannula into the patient's eye is self-sealing upon the removal of the cannula. Particular orientations of the cannula during insertion can aid in self-sealing. The cannula tip can further be configured to have particular beveled designs which further aid in the self-sealing method.

While the delivery apparatus according to the invention facilitates the inventive method of delivering an ocular microimplant, it is not necessary to the practice of inventive method. For example, one skilled in the art can also use a needle and plunger assembly, where the needle has dimensions corresponding to the described cannula.

The methods and apparatus of the invention provide numerous advantages, not least of which is providing for an easier, convenient, and less traumatic means for delivering implants into the eye. In certain embodiments, the self-sealing means of implant delivery can be achieved, which in addition to being less invasive and traumatic, offers less costly treatment by obviating the need for performing the procedure in a surgical setting.

The methods and apparatus of the invention also provide for a more controlled means of delivering implants into the eye. In particular, embodiments of the inventive apparatus are designed to provide a smooth, controlled delivery of the implant. Additional embodiments provide for safety features which include, among other things, user feedback upon the ejection of an implant and locking mechanisms which prevent backflow of eye fluid after ejection and/or which also prevent reuse of the applicator. Another advantage of the inventive apparatus is ease and flexibility of manufacture and assembly of apparatuses for delivery of different implants.

BRIEF DESCRIPTION OF THE DRAWINGS

FIG. 1 depicts a side view of an implant delivery apparatus according to one embodiment of the present invention;

FIG. 2 depicts a top view of the apparatus of FIG. 1;

FIG. 3 depicts a front view of the apparatus of FIG. 1;

FIG. 4 depicts a perspective exploded view of the apparatus of FIG. 1 showing the nose cone disengaged from the housing;

FIG. 5 depicts a perspective exploded view of the nose cone and cannula assembly of the apparatus of FIG. 1;

FIG. 6 depicts a perspective exploded view of the housing, linkage, and actuating lever of the apparatus of FIG. 1;

FIG. 7 depicts an enlarged perspective view of the linkage of the apparatus of FIG. 1;

FIG. 8 depicts an enlarged perspective view of the actuating lever of the apparatus of FIG. 1;

FIG. 9A depicts a side elevated view in section of the apparatus of FIG. 1, showing the linkage, actuating lever and cannula assembly prior to ejection of an implant from the apparatus;

FIG. 9B depicts a side elevated view in section of the apparatus of FIG. 1, showing the linkage, actuating lever and cannula assembly after ejection of an implant from the apparatus;

FIG. 10 depicts a perspective exploded view of an implant delivery apparatus according to another embodiment of the invention, showing different housing, linkage and cannula assemblies;

FIG. 11A depicts a side elevated view in section of the apparatus of FIG. 10, showing the linkage and cannula assembly prior to ejection of an implant from the apparatus;

FIG. 11B depicts a side elevated view in section of the apparatus of FIG. 10, showing the linkage and cannula assembly after ejection of an implant from the apparatus;

FIG. 12A depicts a side elevated view in section, with parts broken away, of an implant delivery apparatus according to yet another embodiment of the invention, showing yet another linkage mechanism and cannula assembly prior to ejection;

FIG. 12B depicts a side elevated view in section of the apparatus of FIG. 12A, with parts broken away, showing the linkage and cannula assembly after ejection of an implant from the apparatus;

FIGS. 13A–B depict top and side views, with parts broken away, of a cannula tip according to one embodiment of the invention; and FIGS. 14A–B depict top and side views, with parts broken away, of a cannula tip according to another embodiment of the invention.

DETAILED DESCRIPTION

An embodiment of an implant delivery apparatus according to the present invention is depicted in FIGS. 1–9. As shown, implant delivery apparatus 10 includes external housing 20 with nose cone 30 attached to and extending from the housing. Cannula 40, having beveled tip 41, extends from the nose cone. Ejector button 50 extends through opening 52 of the housing. As described further herein, an implant can be loaded into the cannula and the apparatus can be readily manipulated to introduce the cannula into a patient's eye at a desired location. Depression of the ejector button actuates the apparatus, and causes the ejection of the implant into the patient's eye.

As used herein, "implants" refers to ocular implants or drug delivery devices which can be implanted into any number of locations in the eye, and which are designed such that a controlled amount of desired drug or therapeutic can be released over time. Such implants are biocompatible, and in many but not all cases are formed of a bioerodible substance, such as a bioerodible polymer. "Microimplants" refers to implants having a sufficiently small cross-sectional area that they can be delivered by methods and/or apparatus according to the invention that result in self-sealing of the eye at the puncture site associated with the delivery. In particular, such microimplants have dimensions such that they are deliverable through 21 gauge or 22 gauge or smaller gauge cannulas. Thin wall versions of 21 gauge needles can be manufactured having inner diameters of up to 0.028 inches, thus cylindrical microimplants deliverable through such sized cannulas will have outer diameters of less than 0.028 inches. Thin wall versions of 22 gauge needles can have inner diameters of up to 0.023 inches, and thus cylindrical microimplants with diameters of less than 0.023 inches will be deliverable through such sized cannulas. Microimplants can also have non-circular cross-sectional geometries for delivery through cannulas having corresponding cross-sectional geometries. Where the micro-implant has non-circular cross-section, the cross-sectional area may be up to 0.00025 square inches or more, depending on the particular cross-sectional geometry.

As used herein, "self sealing" methods of delivering microimplants into the eye refers to methods of introducing microimplants through a cannula and into desired locations of a patient's eye without the need for a suture, or other like closure means, at the cannula puncture site. Such "self sealing" methods do not require that the puncture site completely seal immediately upon withdrawal of the cannula, but rather that any initial leakage is minimum and dissipates in short order such that a surgeon or another equally skilled in the art, in his or her good clinical judgment, would not be compelled to suture or otherwise provide other like closure means to the puncture site.

The apparatus is ergonomically configured for easy gripping and manipulation, and has a general overall shape similar to a conventional pen or other writing instrument. The apparatus will typically be grasped by the user between the thumb and the middle finger. Tactile ridges 22 are provided on the housing, in the areas around the ejector button where the thumb and middle finger of the user are contact the apparatus, to provide a more secure grip and feel to the user. Ejector button 50 itself is provided with tactile grooves 53 on the button surface where the index finger typically contacts the button, also providing for a more secure grip and feel for the user.

As shown more clearly in FIG. 4, nose cone 30 can be manufactured as a separate piece that is then secured to the housing. Specifically, collar 24 extends from the housing as shown. Nose cone 30 is configured for receipt over and attachment to the collar.

As seen in FIG. 5, nose cone 30 receives cannula assembly 42 which consists of cannula 40 and cannula hub 44. The hub is configured for receipt and securement within nose cone 30, with cannula 40 extending through nose cone hole 32. The cannula lumen is in communication with inner passageway 43 of the hub, such that implant 1 can be passed through the inner passageway of the hub and loaded into the cannula lumen. Plunger 46 includes push rod 48 and cone 49. Push rod 48 is configured for slidable receipt within the cannula lumen, and is of sufficient length to displace a loaded implant retained with the cannula lumen and eject it from the cannula tip.

Referring to FIG. 6, it can be seen that housing 20 is formed of two half sections 21 and 22. These sections are preferably configured to snap-fit together, although other known methods of attaching the two halves together are contemplated, including, e.g., gluing, welding, fusing, etc. Alternatively, the housing could be singularly molded. Label plate 23 is also provided, which likewise can be snapped onto or otherwise secured to, the housing. Nose cone 30 can be secured to collar 24 of housing 20 by similar means.

Actuating lever 52 and linkage 60 are retained within housing 20. As seen in FIGS. 6 and 8, actuating lever 52 consists of elongate member 54 having pins 55, 56 extending from the member at one end and ejector button 50 extending from the other end. Pins 55, 56 extend along a common axis and are received in corresponding pivot holes 26 of the housing sections, such that when assembled, the lever can pivot about the pins in a restricted range of motion within the housing.

Linkage 60, as seen more clearly seen in FIG. 7, consists of front and rear blocks 61 and 62, with a plurality of joined segments 63 extending therebetween. The segments are sequentially joined to one another. Flexible joints 64 connect the segments to each other and to the front and rear blocks. The linkage is flexible yet resilient, and preferably formed of a contiguous, moldable plastic piece. Portions of the linkage having a relatively thin cross-sectional area of material form flexible joints 64, and disposed between thicker, less flexible segments 63. This allows for flexure of the linkage at the joint locations when a force is applied to the linkage. Other known materials are also suitable for the linkage, including e.g. shape memory alloys, provided the resultant linkage is capable of lengthwise extension when a force normal to or perpendicular to the length of the linkage is applied.

When assembled, rear block 62 is fixedly secured into slot 27 of the housing, as shown in FIG. 6, and more clearly in FIGS. 9 and 10. Guide pins 65, 66 extend from front block 61 and are received in guide track 28. Guide track 28 is defined by guide ribs 29, 29 that extend inwardly from collar 24. Cone 49 of plunger 46 abuts against front block 61 of the linkage. The linkage, guide track, plunger, cannula, and implant (if loaded within the cannula) are all aligned along the longitudinal axis of the apparatus.

As can be seen, the underside of button 50 of actuating lever 52 is in contact with the linkage (FIG. 9A). In operation, depression of button 50 by the user transmits force against the linkage through underside of button 50 in a direction generally normal to the longitudinal axis of the apparatus. This force is transmitted through the linkage, and is converted into a longitudinal force along the longitudinal axis of the apparatus, through flexure of the linkage joints. Because the rear block end of the linkage remains fixed to the housing, this action results in translational motion of the free, front block end of the linkage in the direction away from the fixed rear block of the linkage. This translational movement of the front block of the linkage in turn pushes push rod 46 through the lumen of cannula 40. Where an implant is loaded and retained within the cannula lumen, the motion of the push rod in turn ejects the implant from the cannula tip (FIG. 9B).

Button 50 also includes tab 57, which is engageable with tab slot 58 of the housing. The tab includes a detent which, when engaged in slot 58 will provide an audible click, signaling the user that the implant has been deployed, and will also retain the actuating lever in a locked, depressed condition, after deployment of the implant.

A second embodiment of an implant delivery apparatus according to the present invention is depicted in FIGS. 10-11. In this embodiment, implant delivery apparatus 110 includes housing 120 with actuator 170 disposed within the housing. The actuator includes linkage 160 formed of two opposing flexible bowing elements 165 and 166. Ridges 171 and 172 are provided on the apexes of the bowing elements, and portions of the bowing elements that include ridges 171 and 172, extend through openings 124 and 125 of the housing. Cannula assembly 142 is secured to the housing. As with the previous embodiment, an implant can be likewise loaded into the cannula. Depression of bowing elements 165 or 166 actuates the apparatus, causing the ejection of the implant from the cannula, as will be further detailed.

Housing 120 is formed of two sections, upper and lower housing sections 121 and 122, that can be assembled as previously described above with respect to the embodiment of FIGS. 1–9. Similarly, apparatus 110 is also ergonomically configured for easy gripping, and will likewise typically be grasped by the user between the thumb and the middle finger. Ridges 171 or 172 include tactile grooves or are otherwise textured to provide for a more secure grip and feel for the user. Additional tactile ridges can be provided on the housing itself in proximity to openings 125 and 126.

Linkage 160 further includes front and rear blocks 161 and 162, and push rod 148 extending from the front block 161. The ends of bowing elements 165 and 166 coincide at front and rear blocks 161 and 162. Suitable materials for linkage 160 are the same as those describe above with respect to linkage 60 of the embodiment of FIGS. 1–9. When assembled, rear block 162 is secured to the housing and retained in a fixed position relative to the housing by tabs 127 and 128. Front block 161 is received and slidable within track 129 on lower housing section 122. Push rod 148 extends from front block 161 and is axially aligned with cannula 140. The push rod can be formed of wire, and in one method of manufacture, the linkage can be molded directly onto a wire and then the wire can be cut to the desired dimensions to form the push rod.

In the undeployed condition, depicted in FIG. 11A, implant 101 is retained in the cannula, distal to the push rod. Manual pressure on bowing element 165 or 166 supplies a normal force to longitudinal axis of the apparatus. This force is transmitted, via flexing of the bowing elements, into a longitudinal force along the longitudinal axis, which in turn causes movement of the free, front block 161 of the linkage away from the fixed, rear block 162. This in turn pushes push rod 146 through the cannula, which in turn ejects a loaded implant from the cannula, as shown in FIG. 11B.

Lock tab 174 is provided on upper housing section 121 and further includes lock stop 175 that is engageable with notch 176 on front block 161. The lock tab itself can be integrally formed with upper housing section 121, and configured such that the lock stop snap-fits into the notch when positioned properly. In operation, as front block 161 moves forward in relation to the housing, angled face 178 engages lock stop 175 and deflects the lock tab upward. The lock tab remains deflected upward until movement of the front block brings notch 176 into position such that lock stop engages the notch. As can be appreciated, the location of the notch relative to the front block length will govern the distance traveled by the push rod in ejecting the implant. In the embodiment shown, the actuator can be inserted into the housing in two different orientations to provide for two different ejection distances for the push rod. As seen, a similar angled face 179 and notch 177 are provided on block 161 opposite face 178 and notch 176, with notch 176 being offset from notch 177 relative to housing longitudinal axis. Therefore, the same actuator can be rotated 180 degrees upon assembly of the apparatus such that lock stop 175 instead engages notch 177, thereby allowing for the push rod to travel an alternate distance govenrned instead by the location of notch 177 relative to the front block length. In the embodiment shown, notch 177 provides for a 1 mm displacement and notch 176 provides for a 2 mm displacement.

A third embodiment of an implant delivery apparatus according to the present invention is depicted in FIGS. 12A-12B. In this embodiment, implant delivery apparatus 210 includes housing 220 and cannula assembly 242. Cannula assembly 242 includes cannula 240 disposed within and extending from nose portion 230, and push rod 248 that is slidably received with the cannula and terminates at its proximal end in cone 249 which is disposed in the interior of the housing. Lever 254 is mounted for movement normal to the longitudinal axis of the apparatus. One end of the lever extends from the apparatus through opening 251 and terminates in button 250. The other end of the lever includes tab 257 which is engageable with latch 258 on housing 220. The tab and latch can be configured to engage in a snap-fit relationship. Cam 260 is disposed within housing 220 and is pivotally mounted to the housing about pivot 265 which is located distally relative to lever 254. Slot 267 is provided on cam 260. Pin 256 on lever 254 is slidably retained within slot 267. The end of cam 260 is located proximal to the cone 249 and push rod 248 assembly.

In the undeployed condition depicted in FIG. 12A, implant 201 is retained in the cannula distal to the push rod. Manual depression of button 250 causes downward movement of lever 254 normal to the longitudinal axis of the apparatus. This movement exerts a force onto cam 260 which is transmitted by way of pin 256 of the lever to slot 267 of the cam, causing rotational movement of cam about pivot 265. With the end of cam 260 in approximation to cone 249, such rotation of the cam causes the end of the cam to engage cone 249, causing translational movement of cone 249 and plunger 248 relative to the housing. This translational movement of the plunger, in turn, ejects the implant from the cannula, as depicted in FIG. 12B. When the lever is fully depressed and the implant ejected, tab 257 engages latch 258, thereby locking the assembly into a depressed, post-ejection, condition.

An advantage of an implant delivery apparatus according to the invention is that it provides for a very smooth, controlled ejection of the implant. By "controlled" it is meant that the force applied to the implant for ejection is proportional to the force applied by the user to actuate the apparatus. The user has direct feedback as to the rate of ejection and can dynamically adjust the force being delivered to the linkage to obtain the desired ejection rate. In addition, depending in particular linkage configurations and dimensions, the apparatus can be configured such that the range of translational movement of the plunger along the longitudinal, or "x" axis, of the housing can be significantly longer, although still proportional to, the range of movement of the actuator along the normal or "y" axis. In such situations, relatively long implants can be effectively delivered by an apparatus that is actuated by a comparatively short actuating stroke. The embodiment of FIGS. 9A & 9B depicts such a situation, where the displacement y of button 50 results in a larger displacement x of plunger 48.

The controlled delivery that can be achieved by the inventive apparatus has additional advantages as well. For example, the controlled delivery provides a more predictable and reproducible placement of the implant, i.e., the implant will tend to be placed at a location very near the cannula tip, and not be projected to a more distant location as may potentially occur with the use of, e.g., a spring-loaded device where a sudden force is instantaneously applied to the implant. The inclusion of locking mechanisms, such as tab 57 and slot 58 locking mechanism of the apparatus of FIGS. 1–9, or the lock tab mechanism of the apparatus of FIGS. 10–11, or the tab-latch mechanism of the apparatus of FIGS. 12A–12B, guards against backflow of eye fluid into the cannula after deployment of the implant. These locking mechanisms can further be configured such that the engagement between the two is irreversible, which prevents reuse of the apparatus. This is advantageous, e.g., if a single-use apparatus is desired.

The combination of the overall housing shape, together with the particular positioning of the tactile ridges in approximation with the actuator position also provides for additional safety advantages. In particular, the design allows the user to control the positioning of the cannula and maintain its stability primarily through manipulation of the thumb and middle finger. The index finger meanwhile controls actuation of the apparatus, and thus the ejection of the implant from the cannula at the desired location. This design effectively separates positioning control from actuation control, and reduces the risk that the step of ejecting the implant will inadvertently cause movement of the device such that the actual placement of the implant is not at the intended location.

The cannulas themselves are in many respects is similar to standard surgical needles, and can be formed of stainless steel in a variety of gauges. The gauge will be chosen such that the inner diameter of the cannula lumen, or bore, will correspond to the outer diameter of the chosen implant, with enough tolerance such that the implant can be received into and subsequently ejected from the cannula lumen. In the embodiment of FIGS. 10 and 11, cannula 140 can be a standard surgical needle having luer lock fitting on its hub, which can be received and secured to a corresponding luer fitting provided on the end of housing 120.

It is desirable, although not necessary, to use a cannula that corresponds in dimensions to a 21 or 22 gauge needle or smaller. Such a small cannula has the important advantage that punctures made by such small bore needle or cannula according to techniques described herein are self-sealing. In the present application, this becomes advantageous in that the implant delivery into the eye can be accomplished without the need for suturing the puncture site, as would be necessary were a larger gauge needle used. We have determined that by using a 21 or 22 gauge cannula or smaller, the implant can be placed and the cannula withdrawn without excessive fluid leakage from the eye, despite the normal fluid pressures within the eye, and stitching of the puncture site can be avoided. 21 gauge needles have outer diameters of approximately 0.032 inches. Thin wall or extra thin wall versions of 21 gauge needles can have inner diameters of approximately 0.023 to 0.026 inches. 22 gauge needles have outer diameters of approximately 0.028 inches, and thin wall or extra thin wall versions of 22 gauge needles have inner diameters of approximately 0.019 to 0.023 inches. Ideally a cannula corresponding in dimensions up to those of 22 or 23 gauge, thin wall needles are used. Microimplants are dimensioned to have outer diameters to be received within the needle cannulaes with sufficient tolerances to be readily pushed through the cannula. For example and without being so limited, microimplants with a diameter of 0.018 inches can be easily delivered through a 22 gauge thin wall needle, and a microimplant with a diameter of 0.015 inches is easily deliverable through a 23 gauge thin wall needle. The invention further contemplates the use of cannulas having non-circular cross-sections, including oval or elliptical cross-sections. For such non-circular cross-sectional cannulas, it is desirable that the cross-sectional area correspond to that of a circular cannula having up to a 0.032 inch diameter, that is, a cross-sectional area up to 0.0008 square inches or more, depending on the particular cross-sectional geometry.

In addition to cannula dimensions, additional modifications to both the cannula tip and in particular methods of insertion can further aid successful self-sealing methods of implantation. A typical problem when inserting a cannula into any tissue is the phenomena of "coring" of the tissue, where the insertion actually cuts a cylindrical section of tissue that enters the cannula lumen. Such coring when it occurs in the eye can exacerbate leakage of eye fluid through the injection site. By approaching the eye tissue at more of an angle relative to normal, there is a better opportunity for the cannula tip penetrate and separate through the tissue layers and reduce coring of the tissue. Additional techniques to further reducing coring and/or excessive leakage are further described herein.

The cannula tip itself also can be configured to reduce coring phenomena, for instance, by sharpening certain portions of the bevel tip and dulling others. FIGS. 12A and 12B depict one such embodiment, where cannula tip 40a includes side bevels 31a, 32a that extend distally of designated line L1 and constitute approximately one half of the bevel tip and dulled area 33a extending proximally of line L1, constituting the other half of the bevel tip. The dulled area 33a can be created through conventional polishing techniques known in the art. FIGS. 13A and 13B depict another such embodiment, where cannula tip 40b that also includes side bevels 31b and 32b extending distally of designated line L2 and dulled area 33b extending proximally of line L2. However, in this embodiment, the side bevels 31b, 32b constitute only about one quarter or less of the bevel tip. In each of these embodiments, the sharp side bevels allow for an initial piercing of tissue, but as the tip is further inserted the tissue encounters the dulled areas of the bevel tip, which do not have sharp cutting edges, thus promoting separation of tissue layers as the cannula is advanced and mitigating against further cutting and possible coring of the tissue. In addition to these designs, conventional needle tips have also proven satisfactory.

One skilled in the art will appreciate that the particular site of entry and the distance the cannula is inserted will depend on the particular application and the desired final location of the implant. As can also be appreciated, the ability provided herein to provide for a self-sealing method for delivering implants, has enormous impact on the ability of physicians and healthcare workers to treat diseases of the eye, because it obviates in most situations the necessity of surgery facilities, and accompanying surgical support, currently required by conventional methods.

To administer an implant using, e.g., the implant delivery apparatus of FIGS. 1–9, the user can grasp apparatus 10 between the thumb and middle finger along tactile ridges 22, and position the apparatus near the desired point of entry into the patient's eye. The patient typically will be under a topical or local anesthetic. The user can then advance cannula 40 into the patient's eye to the desired depth, and depress ejector button 50 to eject the implant at the desired location. The cannula 40 is then withdrawn. Specific techniques for cannula advancement, including angles of orientation of the cannula and the bevel are further discussed herein. Where cannula 40 is dimensioned to receive and retain a microimplant, as previously discussed, the resultant puncture site can self-seal upon withdrawal of the cannula. Otherwise, in situations where a larger cannula and implant are used, the puncture site can be closed up by known methods, such as suturing.

Self-sealing methods can also be performed without the inventive apparatus, albeit less conveniently. In such a method, a cannula having dimensions corresponding to those described above can be provided attached to a suitable holder, such as, e.g., a typical needle and syringe assembly. The microimplant is loaded and retained within the cannula lumen, and a push rod is further provided with the distal end received through the proximal end of the cannula lumen and positioned adjacent the microimplant. The distal end of the push rod remains outside the cannula and manually accessible. This assembly is then brought into position near the patient's eye, and the cannula is then used to puncture through the outer layer of a patient's eye and the cannula is further advanced a desired location within the patient's eye for deposition of the microimplant. Once the cannula is positioned, the push rod is moved from the proximal end of the cannula toward the distal end of the cannula, thereby ejecting the microimplant from the cannula. After ejection, the cannula and push rod are withdrawn from the patient's eye, and the puncture created by the insertion of the cannula into the patient's eye is self-sealing upon the removal of the cannula.

For placement e.g. in the vitreous cavity of the eye, useful implantation methods include advancing the needle through the pars plana at a location approximately 3.5–4 mm from the limbus of the eye. For smaller diameter needles, e.g., 25 gauge or smaller, the needle can be inserted from any angle relative to the eye and still produce acceptable self-sealing results. For larger gauge needles, e.g., 23 gauge and above, self-sealing results can be enhanced by inserting the needle at angle relative to the eye surface. For example, good results are achieved by inserting the angle at an angle of 45° or less relative to the eye surface. Also, slightly improved results can be seen in some cases by orienting the bevel of the needle downward with respect to the eye surface. Another advantageous method involves a so-called "tunnel technique" approach. In this technique, the patient's eye is restrained from moving using e.g. a cotton swab or forceps, and the needle is advanced into the sclera at an angle approaching parallel relative to the eye surface. In this technique, the bevel will usually be oriented upward with respect to the eye surface. Once the tip is advanced sufficiently far enough into the scleral layer, usually such that the bevel portion is at least disposed within the scleral layer, the angle of the needle is adjusted to a more downward angle into the eye, and the needle is further advanced. Using such methods, with the shallower angle of insertion, yields wound edges that close up and seal more readily. Without being bound by theory, it is believed that insertion of the needle by this technique creates a scleral "flap" that, under intraocular pressure of the eye, is forced upward and pressed against the wound path to more effectively close up the wound.

In addition, the direction of insertion of the needle relative to the limbus of eye can have further implications upon the deposition of the implant in the vitreous cavity. For example, advancement of the needle posteriorally of the limbus or even circumferentially relative to the limbus usually provides for a suitable and acceptable location for deposition of the implant. On the other hand, advancement of the needle anteriorally of the limbus requires some caution, as it can lead to placement of the implant close to the lens of the eye, which may cause some complications.

Implants that are compatible with loading and ejection from apparatus according to the present invention can be formed by a number of known methods, including phase separation methods, interfacial methods, extrusion methods, compression methods, molding methods, injection molding methods, heat press methods and the like. Particular methods used can be chosen, and technique parameters varied, based on desired implant size and drug release characteristics. For microimplants described herein, which can be delivered through cannulas corresponding to a 21 gauge needle or smaller, and which therefore have cross-sectional diameters of 0.026 inches or less, or similar cross-sectional areas, extrusion methods are particularly useful. Extrusion methods, as well as injection molding, compression molding, and tableting methods, can all achieve the small cross-sectional diameters or areas required of microimplants. Extrusion methods also may result in more homogenous dispersion of drug within polymer, which can be important given the small dimensions of microimplants.

As previously mentioned, microimplants that have diameters of 0.018 inches or less are deliverable through 22 gauge thin-walled cannulaes, and microimplants with diameters of 0.015 inches or less are deliverable through 23 gauge thin-walled cannulaes. Because of the extremely small cross-sectional diameters or areas of these microimplants, the corresponding length will need to proportionally larger to provide desired therapeutic dosages of many active agents. Typically, the microimplants can be manufactured so as to extend up to about 6 or 7 mm in length or longer. A microimplant of 7 mm or less in length may be preferable, at least for placement in the vitreous, as implants of greater length may interfere with a patient's vision.

In manufacturing an implant delivery apparatus according to the invention, it may be desirable to pre-load the implant into the cannula. Pre-loaded apparatus provide added convenience for the user and avoid unnecessary handling of implants. Further, such loading can be done under sterile conditions, thereby ensuring delivery of a sterilized implant. For the embodiment of FIGS. 1–9, the implant can be pre-loaded into the cannula assembly and the loaded cannula assembly incorporate into the nose cone. In this fashion, loaded nose cone/cannula assemblies can be pre-assembled, for later incorporation with the housing assembly. Similarly, for the embodiment of FIGS. 10–11, the implant can be preloaded in the cannula and then later assembled onto the housing assembly. In an alternative variation on this embodiment, the cannula can have two separate parts, with one part of the cannula retained within the housing that then communicates with the other external portion of the cannula that is subsequently connected to the housing. In such a variation, an implant can further be preloaded in the cannula part retained within the housing. In any case, push rods and linkages of the appropriate lengths are provided dependent on the length of the particular loaded implant, such that complete ejection of the particular implant can be assured.

Label plates, or other locations on the housing, can include the appropriate information relative to particular implant loaded. Given this interchangeability, unique apparatus for the delivery of selected implants can be easily manufactured, simply by providing the particular cannula, plunger, and linkage system for the selected implant. The remaining components of the apparatus remain the same.

The name plate or housing itself can be labeled to correspond to the selected implant, thus identifying the apparatus with the loaded implant.

When the apparatus is assembled with the implant preloaded, it may further be desirable that the implant be positioned just proximal of the opening at the cannula tip. In this fashion, the introduction of air into the eye can be avoided when the implant is ejected, as could otherwise occur were the implant located further within the cannula lumen and an air bubble or air pocket allowed to exist between the cannula tip and the implant and ejection of the implant were to force the air bubble or air pocket into the eye. One method to accomplish this is to load the implant distally into the cannula followed by the plunger, with the plunger length designed to push the implant to the desired pre-actuation position. When the cannula assembly is then installed onto the housing, the plunger and thus the implant is advanced to the desired position. To guard against inadvertent premature release of the implant, the cannula can have a slight bend incorporated into the tip such that enough friction exists between the inner wall of the cannula and the implant to hold the implant in place, but at the same time, the frictional force is easily overcome by action of the plunger to eject the implant upon actuation of the apparatus.

Other cannula designs can likewise achieve the desired effect of avoiding the introduction of air into the eye upon ejection of the implant. For example, the implant can be positioned proximally of the cannula tip but with sufficient tolerance between the implant and cannula wall to provide for air exhaust past the implant as it is moved through the cannula. Adequate tolerances are those that retain air in front of the implant at close to ambient pressure as the implant is moved along the cannula. Because fluid pressure within the eye is typically slightly positive relative to ambient pressure, air at ambient pressure will not enter the eye.

Loaded apparatus according to the invention can be packaged to include a safety cap extending over the cannula and securing to the housing. This will provide a measure of safety during handling of the apparatus. The button or other depression mechanism of the apparatus can also include a notch which receives the rim of the safety cap. In this configuration, the safety cap will then also operate to guard against unintentional depression of the button or other depression mechanism and ejection of the implant.

As can be appreciated, an implant delivery apparatus according to the invention that is provided loaded with the desired implant is of great benefit to the physician user. Such apparatus can be provided sterile packaged for a single use application. The user need not ever handle the implant itself. As previously mentioned, the apparatus provides for a controlled ejection of the implant. The configuration and design of the apparatus also helps to achieve uniform placement of implants from patient to patient. Further, when the apparatus is configured to deliver a micro-implant, the apparatus provides a self-sealing method for delivery, as previously discussed. This has enormous benefit to the physician and patient in that the entire implant procedure can safely, easily, and economically be performed in a physician's office, without the need for more costly surgical support currently required for implant delivery.

The invention is further illustrated by the following non-limiting examples.

EXAMPLES

Example 1

Effects of Needle Size and Technique on Vitreous Leakage

Different gauge needles together with various insertion techniques were pursued to determine the maximum size needle gauge and optimum insertion technique for mimimum vitreous leakage and "self-sealing" wounds.

Eight rabbits were anaesthetized with a Ketamine/Xylazine cocktail. Drops of a 0.5% Opthaine solution were delivered to each eye of the rabbit as a local anaesthetic. 16 g, 20 g, 22 g, 23 g, 25 g needles (Beckton-Dickinson, Franklin Lakes, N.J.) were attached to syringes and inserted into the vitreous cavities of the rabbits' eyes, through the pars plana (2–3 mm from the limbus) according to varying techniques. For each needle size, the needles were inserted at either angles of 90° or 45° relative to the pars plana of the eye, or according to the following "tunnel" technique. In the "tunnel" technique, the needle is initially advanced into the first scleral layer of the eye tissue at a very shallow angle, almost parallel, to the sclera. Once the needle has penetrated sufficiently, usually to a position whereby the bevel has passed into the scleral layer, the orientation of the needle is adjusted and further advanced at a sharper angle of attack, for example, typically anywhere up to 45°. Table 1A below details the needle gauge and insertion technique for each animal.

TABLE 1A

STUDY DESIGN

| Animal | Eye | Needle size | Bevel position, insertion orientation |
|---|---|---|---|
| 1 | OD | 16 g | Up, 90° |
|   | OS | 16 g | Down, 90° |
| 2 | OD | 20 g | Up, 90° |
|   | OS | 20 g | Down, 90° |
| 3 | OD | 22 g | Up, 90° |
|   | OS | 22 g | Down, 90° |
| 4 | OD | 23 g | Up, 90° |
|   | OS | 23 g | Down, 90° |
| 5 | OD | 25 g | Up, 90° |
|   | OS | 25 g | Down, 90° |
| 6 | OD | 23 g | Up, 45° |
|   | OS | 23 g | Down, 45° |
| 7 | OD | 23 g | Tunnel technique |
|   | OS | 23 g | Tunnel technique |
| 8 | OD | 22 g | Tunnel technique |
|   | OS | 22 g | Tunnel technique |

OD - right eye,
OS - left eye

Upon removal of each needle from the eye, the resulting wounds were examined and observations of wound shape and characteristics and amount of vitreous were recorded.

The results are tabulated in Table 1B below.

TABLE 1B

OBSERVATIONS

| Animal | Eye | Needle size (gauge) | Bevel position, orientation | Observed Leakage | Wound description and characterization |
|---|---|---|---|---|---|
| 1 | OD | 16 | Up, 90° | +++ | Big, round, not sealing after swab, suture needed |
|   | OS | 16 | Down, 90° | +++ | Big, round, not sealing after swab, suture needed |
| 2 | OD | 20 | Up, 90° | +++ | Big, round, not sealing after swab |
|   | OS | 20 | Down, 90° | +++ | Big, round, not sealing after swab |
| 3 | OD | 22 | Up, 90° | +++ | Round, not sealing after swab |
|   | OS | 22 | Down, 90° | + | Round, not sealing after swab |
| 4 | OD | 23 | Up, 90° | ++ | Round, not sealing after swab |
|   | OS | 23 | Down, 90° | + | Round, not sealing after swab |
| 5 | OD | 25 g | Up, 90° | no leakage − | Very small, round, sealed after swab |
|   | OS | 25 g | Down, 90° | Minimum ± | Very small round, not sealed after swab |
| 6 | OD | 23 g | Up, 45° | Minimum ± | Almost sealed, edges close |
|   | OS | 23 g | Down, 45° | no leakage − | Almost sealed, edges close |
| 7 | OD | 23 g | Tunnel technique | no leakage − | perfectly sealed |
|   | OS | 23 g | Tunnel technique | no leakage − | perfectly sealed |
| 8 | OD | 22 g | Tunnel technique | Minimum ± | sealed |
|   | OS | 22 g | Tunnel technique | Minimum ± | sealed |

OD - right eye,
OS - left eye
+++ = severe leakage
++ = substantial leakage
+ = some amount of leakage
+/− = minimum amount of leakage = no leakage Based on the above and additional observations, it can be concluded that insertion technique as well as needle size are important factors in determining wound characteristics and subsequent wound leakage. For the 25 gauge needles, the angle or technique of insertion was less important, with the would be being relatively small, sealed, and demonstrating minimal to no leakage. For larger gauge needles, insertion techniques become more important, insertion of the needle at angles less than normal, i.e., less than 90°, dramatically reduced the amount of leakage and the ability of the wound to sealf seal was enhanced. Insertion by the above-described tunnel technique gave the most promising results, but even a direct approach at an angle under 45° provides very good results. Additionally, slightly better results were obtained with the bevel facing downward relative to the eye tissue upon insertion. Thus it is expected that self-sealing is achievable with 23 gauge or larger needles, including 22 and 21 gauge needles, using the described techniques.

Example 2

Delivery of Microimplants

Cylindrical microimplants having dimensions of 0.015 inches diameter and 6 mm length were delivered into posterior segments of rabbits' eyes using a 23 gauge thin wall needle and according to insertion techniques described above in Example 1.

Four rabbits were anaesthetized as before with a Ketamine/Xylazine cocktail and with drops of a 0.5% Opthaine solution administered to each eye of the rabbit as a local anaesthetic. 23 g thin wall needles (BD, Franklin Lakes, N.J.) were attached to syringes and the needle cannulaes were loaded with the microimplants. The needles were inserted into the vitreous cavities of the rabbits' eyes, according to varying techniques detailed in Example 1 and as further described herein. Table 2A below details the needle gauge and insertion technique for each animal.

TABLE 2A

STUDY DESIGN

| Animal | Eye | Bevel position, orientation of needle |
|---|---|---|
| 1 | OD | Up, 90° |
|   | OS | Down, 90° |
| 2 | OD | Up, 45° |
|   | OS | Down, 45° |
| 3 | OD | Up, 45° |
|   | OS | Down, 45° |

TABLE 2A-continued

STUDY DESIGN

| Animal | Eye | Bevel position, orientation of needle |
|---|---|---|
| 4 | OD | Tunnel technique |
|   | OS | Tunnel technique |

OD - right eye, OS - left eye

In addition to the angle of insertion and the bevel orientation, different orientations of the needles relative to the limbus of the eye were also examined for situations where the needle was inserted at an angle other than normal, i.e., 90°. More specifically, the needles advanced into the eye in (1) a circumferential fashion, that is, along a direction generally tangential to the limbus, (2) a posterior manner, that is, the needle is advanced generally towards the posterior of the eye, and (3) in an anterior manner where the needle advanced toward the anterior of the eye.

Upon insertion of the needle, the microimplants were delivered into the vitreous cavity of the posterior segment by advancing a push wire through the needle cannula to push the microimplants through the needle cannula. The needle was then removed and the resulting wound was examined and observations of wound shape and characteristics and amount of vitreous leakage were recorded. The results are tabulated in Table 2B below. Observations were also made as to location and condition of the delivered implant.

TABLE 2B

OBSERVATIONS

| Animal | Eye | Bevel position, orientation, direction | Leakage | Wound description | DDS disposition |
|---|---|---|---|---|---|
| 1 | OD | Up, 90° | + | Round, not quite sealed after swab | Adequate |
|   | OS | Down, 90° | + | Round, not quite sealed after swab | Adequate |
| 2 | OD | Up, 45° circumferentially | ± | Almost sealed | Adequate |
|   | OS | Down, 45° circumferentially | − | DDS in the wound, after removing almost sealed | Small piece in the wound |
| 3 | OD | Up, 45° posteriorly | − | Almost sealed, edges close | DDS broken into 2 pieces |
|   | OS | Up, 45° anteriorly | − | Almost sealed, edges close | DDS touch the lens |
| 4 | OD | Tunnel Technique circumferentially | − | Sealed | Very close to pars plana and anterior vitreous |
|   | OS | Tunnel Technique circumferentially | − | Sealed | Very close to pars plana and anterior vitreous |

+/− = minimum amount of leakage = no leakage

From the above and additional observations it can be expected that insertion of the needle at an angle of 45° or less gave satisfactory results with respect to self-sealing and likewise resulted in satisfactory placement of the implant. While the previously described tunnel technique provides for the best self-sealing results, the positioning of the implant was slightly less controllable than that observed by a methods where the needle was advanced along a single path. Also, the orientation of the needle relative to the limbus can be important. For example, needles advanced into the eye circumferentially or posteriorly provide for a more advantageous deposition of the implant, whereas needles advanced anteriorly can result in placement of the implant close to the lens which may cause complications. Other difficulties observed in placement of the implants were caused in one instance by breakage of implants during loading such that small pieces of implant were located in the wound. Such occurrences are easily alleviated through increased care in loading the implant and ensuring that the push wire is long enough to completely eject the implant.

While preferred apparatus and methods have been described, the skilled artisan will appreciate that obvious modifications can be made that are within the scope of the invention, as defined in the appended claims.

We claim:

1. An apparatus for injecting an ocular implant into a patient's eye, comprising:
    an elongate housing having a longitudinal axis;
    a cannula extending longitudinally from the housing, the cannula having a lumen extending therethrough and being configured to receive an ocular implant within the cannula lumen;
    a plunger having a push rod receivable within the cannula lumen and moveable from a first to second position; and
    a linkage operably linked to said plunger, the linkage having a moveable end engageable with the plunger, and a fixed end secured to the housing, the moveable end of the linkage being capable of movement from a first to a second position relative to the housing upon application to the linkage of a force perpendicular to the longitudinal axis of the housing, thereby moving the push rod from the first to the second position.

2. The apparatus of claim 1 wherein the moveable end of the linkage is capable of translational motion along the longitudinal axis of the housing.

3. The apparatus of claim 1 further comprising an ocular implant located within the lumen cannula.

4. The apparatus of claim 3 wherein said implant is a microimplant.

5. The apparatus of claim 1 further comprising an actuating lever engageable with said linkage.

6. The apparatus of claim 5 wherein the actuating lever is pivotally mounted within said housing.

7. The apparatus of claim 5 wherein said actuating lever further includes a button extending from the housing for manual depression of the lever.

8. The apparatus of claim 1 wherein said linkage further comprises a plurality of flexibly joined segments.

9. The apparatus of claim 1 wherein said linkage further comprises one or more flexible bow elements.

10. The apparatus of claim 9 wherein a portion of at least one of the flexible bow elements extends from the housing for manual depression.

11. The apparatus of claim 1 wherein said linkage further comprises a cam assembly.

12. The apparatus of claim 1 wherein the cannula has an outer diameter of approximately 0.032 inches or less.

13. The apparatus of claim 1 wherein the cannula has an outer diameter of approximately 0.028 inches or less.

14. The apparatus of claim 1 wherein the cannula has a cross-sectional area of approximately 0.0008 square inches or less.

15. An apparatus for implanting an ocular implant into a patient's eye, comprising:
   an elongate housing having a longitudinal axis;
   a cannula extending longitudinally from the housing, the cannula having a lumen extending therethrough;
   a plunger having a push rod received within the cannula lumen and in engagement with the implant, the plunger moveable from a first to second position; and
   a linkage having a moveable end connected to the plunger, and a fixed end secured to the housing,
   an actuating lever having a first end pivotally mounted within the housing, and a second end in engagement with the linkage,
   wherein movement of the second end of the actuating lever against the linkage in a direction perpendicular to the longitudinal axis of the housing causes translational movement of the moveable end of the linkage from a first to second position parallel to the longitudinal axis of the housing, thereby moving the plunger from the first to the second position and ejecting the implant from the cannula.

16. The apparatus of claim 15 further comprising an ocular implant located within the lumen cannula.

17. The apparatus of claim 16 wherein said implant is a microimplant.

18. The apparatus of claim 15 wherein said actuating lever further comprises a button extending from the housing for manual depression of the lever.

19. The apparatus of claim 15 wherein the cannula has an outer diameter of 0.032 inches or less.

20. The apparatus of claim 15 wherein the cannula has an outer diameter of approximately 0.028 inches or less.

21. The apparatus of claim 15 wherein the cannula lumen has a cross-sectional area of 0.0008 square inches or less.

* * * * *